(12) United States Patent
Nelson et al.

(10) Patent No.: US 6,403,006 B1
(45) Date of Patent: *Jun. 11, 2002

(54) PROCESS OF MAKING DIMENSIONALLY STABLE POLYESTER YARN FOR HIGH TENACITY TREATED CORDS

(75) Inventors: Charles Jay Nelson, Chesterfield; Jayendra Hiralal Bheda; Peter Bryan Rim, both of Midlothian, all of VA (US); James Michael Turner, Cary, NC (US)

(73) Assignee: AlliedSignal Inc., Morristown, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/571,843

(22) Filed: May 16, 2000

Related U.S. Application Data

(63) Continuation of application No. 08/844,744, filed on Apr. 21, 1997, now abandoned, which is a continuation of application No. 08/527,295, filed on Sep. 12, 1995, now Pat. No. 5,630,976, which is a continuation of application No. 08/200,853, filed on Feb. 22, 1994, now abandoned, which is a continuation of application No. 08/110,471, filed on Aug. 23, 1993, now abandoned, which is a continuation of application No. 07/810,600, filed on Dec. 19, 1991, now abandoned, which is a division of application No. 07/237,348, filed on Aug. 29, 1988, now abandoned, which is a continuation-in-part of application No. 07/215,178, filed on Jul. 5, 1988, now abandoned.

(51) Int. Cl.$^7$ .......................... D01D 5/088; D01D 5/12; D01F 6/62
(52) U.S. Cl. .............................. 264/210.8; 264/211.15; 264/211.17; 264/237
(58) Field of Search .................... 264/210.8, 211.15, 264/211.17, 237

(56) References Cited

U.S. PATENT DOCUMENTS

| | | | |
|---|---|---|---|
| 3,690,362 A | 9/1972 | Mago et al. | 152/556 |
| 4,101,525 A | 7/1978 | Davis et al. | 528/308 |
| 4,195,052 A | 3/1980 | Davis et al. | 264/210.5 |
| 4,251,481 A | 2/1981 | Hamlyn | 264/210.3 |
| 4,414,169 A | 11/1983 | McClary | 264/210.7 |
| 4,491,657 A | 1/1985 | Saito et al. | 528/308.1 |
| 4,690,866 A | 9/1987 | Kumakawa et al. | 428/364 |

FOREIGN PATENT DOCUMENTS

| | | |
|---|---|---|
| EP | 0 080 906 | 6/1983 |
| EP | 0 089 912 | 9/1983 |
| EP | 169415 B1 | 10/1988 |
| JP | 35-3104 | 4/1960 |
| JP | 46-28979 | 8/1971 |

(List continued on next page.)

OTHER PUBLICATIONS

Korean Patent Invalidation Trial Brief filed Oct. 8, 1998 by Korean Chemical Fiber Association.
Measurements and Analyses of Fibers by Ro–Soo Kim et al. dated 1990.
Korea Science Promotion Foundation Translation Series 53 Physical Polymer Science dated Mar. 1996.
Korean Industry Property Tribunal Decision dated Nov. 30, 1999.
After Appeal, First Korean Brief filed Apr. 21, 2000 by AlliedSignal Inc.
J. Shimizu et al., "High Speed (Melt) Spinning of Polyethylene Terephthalate Fibers and The Effect of Molecular Weight", Seni Gakkaishi V 34 (1978).
G.W.Davis et al., "Polyester Fibers: Variants", Fiber Producer, pp. 45–62 (Jun. 1984).
A. Roos, "Melt Spinning of PET Industrial Fibers", Fiber Formation Symposium, ACS Meeting, Toronto, Canada (Jun. 5–10, 1988).
Richard Dean, "New Polyester Tire Cord Developments", Polyester Textiles, Shirley Pub S51 (1988).
Opposition Statement by Rhone–Poulenc dated Feb. 22, 1993.
Opposition Statement by Hoechst dated Feb. 26, 1993.
Minutes of European Oral Proceedings dated Apr. 19, 1995.
Minutes of European Technical Board of Appeal Maintaining Patent dated Sep. 23, 1999.
Japanese Opposition Statement filed by Korean Synthetic Fiber Association dated Dec. 27, 1999.
Japanese Patent Office Decision on aforementioned Opposition dated Nov. 9, 2000.
H.H. George et al., "A Study of Structural Development in the High Speed Spinning of Poly(Ethylene Terephthalate)", Polymer Engineering and Science, vol. 23 (2), 95 (1983).
"A Study of Structural Development in the High Speed Spinning of Poly(Ethylene Terephthalate)" by H.H. George, A. Holt, and A. Buckley; Polymer Engineering & Science Mid–Feb. 1983, vol. 23 No. 2, pp. 95–99.
"High Speed Spinning of Polyethylene Terephthalate (PETP) by Pneumatic Take–up. Physical and Mechanical Properties of Filaments" by G. Perez and C. Lecluse, International Chemifasertagung in Dornbirn Conference, Jun. 20–22, 1979, conference pp. 1–37.
International Search Report for PCT/US 89/02781 (Oct. 23, 1989).

*Primary Examiner*—Leo B. Tentoni
(74) *Attorney, Agent, or Firm*—Melanie L. Brown; Virginia Szigeti Andrews; Roger H. Criss

(57) ABSTRACT

Polyethylene terephthalate yarn is prepared by spinning under high stress conditions in the transition region between oriented-amorphous and oriented-crystalline undrawn yarns by selection of process parameters to form an undrawn yarn that is a crystalline, partially oriented yarn with a crystallinity of 3 to 15 percent and a melting point elevation of 2 to 10° C. The spun yarn is then hot drawn to a total draw ratio between 1.5/1 and 2.5/1 with the resulting properties: (A) a terminal modulus of at least 20 g/d, (B) a dimensional stability defined by $E_{4.5}+FS<13.5$ percent, (C) a tenacity of at least 7 grams per denier, (D) a melting point elevation of 9 to 14° C., and (E) anamorphous orientation function of less than 0.75. The resulting treated tire cord provides high tenacity in combination with improved dimensional stability.

5 Claims, 11 Drawing Sheets

U.S. PATENT DOCUMENTS

| | | | |
|---|---|---|---|
| 4,827,999 A | 5/1989 | Yabuki et al. | 152/451 |
| 4,867,936 A | 9/1989 | Buyalos et al. | 264/210.6 |
| 4,975,326 A | 12/1990 | Buyalos et al. | 428/373 |
| 5,132,067 A | 7/1992 | Nelson et al. | 264/210.8 |
| 5,350,632 A | 9/1994 | Lang | 428/382 |

FOREIGN PATENT DOCUMENTS

| | | |
|---|---|---|
| JP | 51-96521 | 8/1976 |
| JP | 58-203112 | 11/1983 |
| JP | S58-203112 | 11/1983 |
| JP | 59-116414 | 7/1984 |
| JP | 59-19812 | 1/1986 |

← = MELTING POINT

PROCESS OF MAKING DIMENSIONALLY STABLE POLYESTER YARN FOR HIGH TENACITY TREATED CORDS

This application is a continuation of application Ser. No. 08/844,744 filed Apr. 21, 1997 (abandoned), which is a continuation of application Ser. No. 08/527,295 filed Sep. 12, 1995 (U.S. Pat. No. 5,630,976), which Ser. No. 09/571,843 filed May 16, 2000 is a continuation of application Ser. No. 08/200,853 filed Feb. 22, 1994 (abandoned), which is a continuation of application Ser. No. 08/110,471 filed Aug. 23, 1993 (abandoned), which is a continuation of Ser. No. 07/810,600 filed Dec. 19, 1991 (abandoned) which is a divisional of Ser. No. 07/237,348 filed Aug. 29, 1988 (abandoned), which is a continuation-in-part of Ser. No. 07/215,178 filed Jul. 5, 1988 (abandoned).

BACKGROUND OF THE INVENTION

1. Field of the Invention

This invention relates to polyester multifilament yarn with high modulus and low shrinkage particularly useful for the textile reinforcement of tires. The yarn of the invention provides high treated cord tenacity while maintaining or increasing treated cord dimensional stability when compared to prior art yarns. A process for,production of the multifilament polyester yarn is an aspect of the invention.

2. Description of the Prior Art

Polyethylene terephthalate filaments of high strength are well known in the art and are commonly utilized in industrial applications including tire cord for rubber reinforcement, conveyor belts, seat belts, V-belts and hosing.

Continued improvement in high strength industrial yarns particularly suited for use as fibrous reinforcement in rubber tires is an ongoing need in the industry. In particular, the improvement of treated cord tenacity and dimensional stability are desired objectives. U.S. Pat. No. 4,101,525 to Davis et al. provides an industrial strength multifilament polyester earn with high initial modulus and low shrinkage. Although Davis et al. does not provide treated cord data, it is commonly known that compared to conventional tire cords such yarn provides a reduced tenacity when the yarn is converted to the treated tire cord. Additionally, rapid cooling of the filament immediately after emerging from the spinneret can result in excessive filament breakage and thus yield yarn with poor mechanical quality. U.S. Pat. No. 4,491,657 to Saito et al. discloses high modulus, low shrinkage polyester yarn, but requires a low terminal modulus to achieve good yarn to treated cord conversion efficiency for such dimensionally stable yarns. The low terminal modulus is carried over into the treated cord and results in a lower tenacity than the high terminal modulus cords of the present invention. Also, as shown in FIG. 8, the process of Saito et al. requires high spinning speeds, which makes it difficult to process on-panel, i.e. a continuous spin-draw process.

SUMMARY OF THE INVENTION

Polyethylene terephthaleate yarn can be prepared by spinning under high stress conditions in the transition region between oriented-amorphous and oriented-crystalline undrawn yarns. The invention is accomplished by selection of process parameters to form an undrawn yarn that is a crystalline, partially oriented yarn with a crystallinity of 3 to 15 percent and a melting point elevation of 2 to 10° C. The spun yarn is then hot drawn to a total draw ratio between 1.5/1 and 2.5/1 with the resulting unique combination of properties: (A) a terminal modulus of at least 20 g/d, (B) a dimensional stability defined by $E_{4.5}+FS<13.5$ percent, (C) a tenacity of at least 7 grams per denier, (D) a melting point elevation of 9 to 14° C., and (E) an amorphous orientation function of less than 0.75. The drawn yarn is twisted and plied to produce tire-cord and then treated with resorcinol-formaldehyde-latex. The resulting treated tire cord unexpectedly provides high tenacity in combination with improved dimensional stability.

DESCRIPTION OF THE PREFERRED EMBODIMENT

Figure 1:
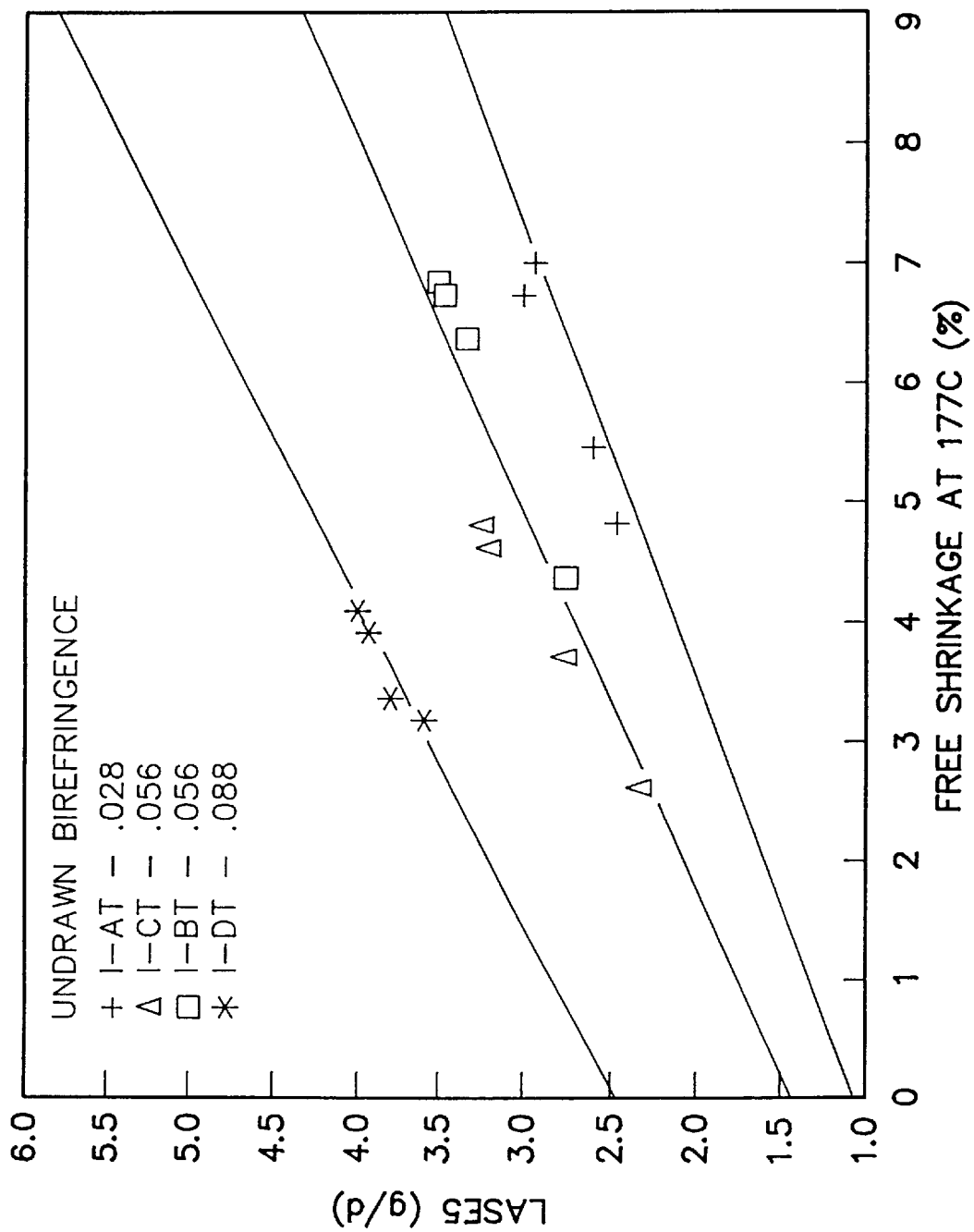
FIG. 1 represents treated cord dimensional stability as judged by plots of LASE-5 versus free shrinkage for the yarns prepared in Example I.
Figure 2:
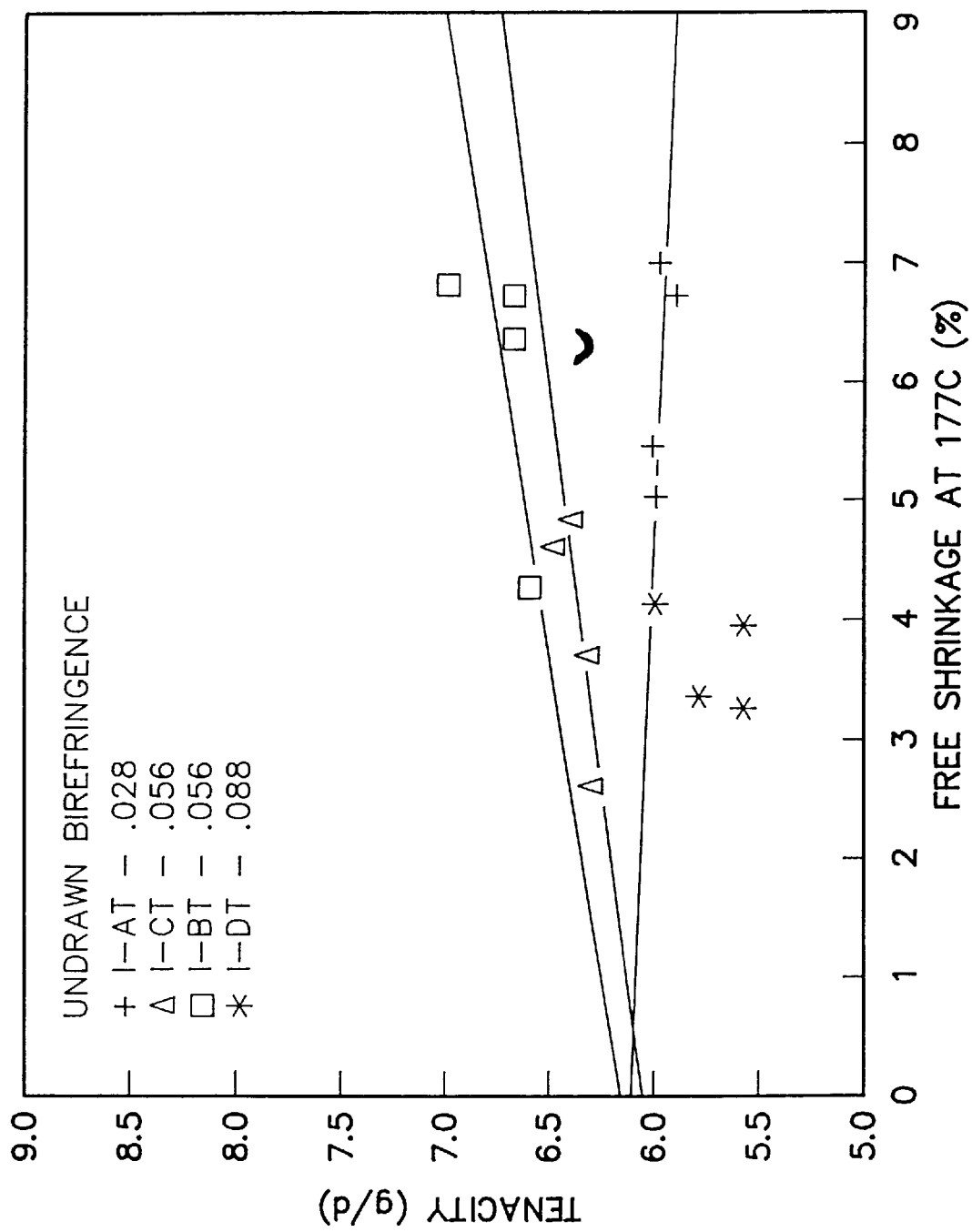
FIG. 2 represents a comparison of treated cord tenacities at a given free shrinkage for the yarns of Example I.
Figure 3:
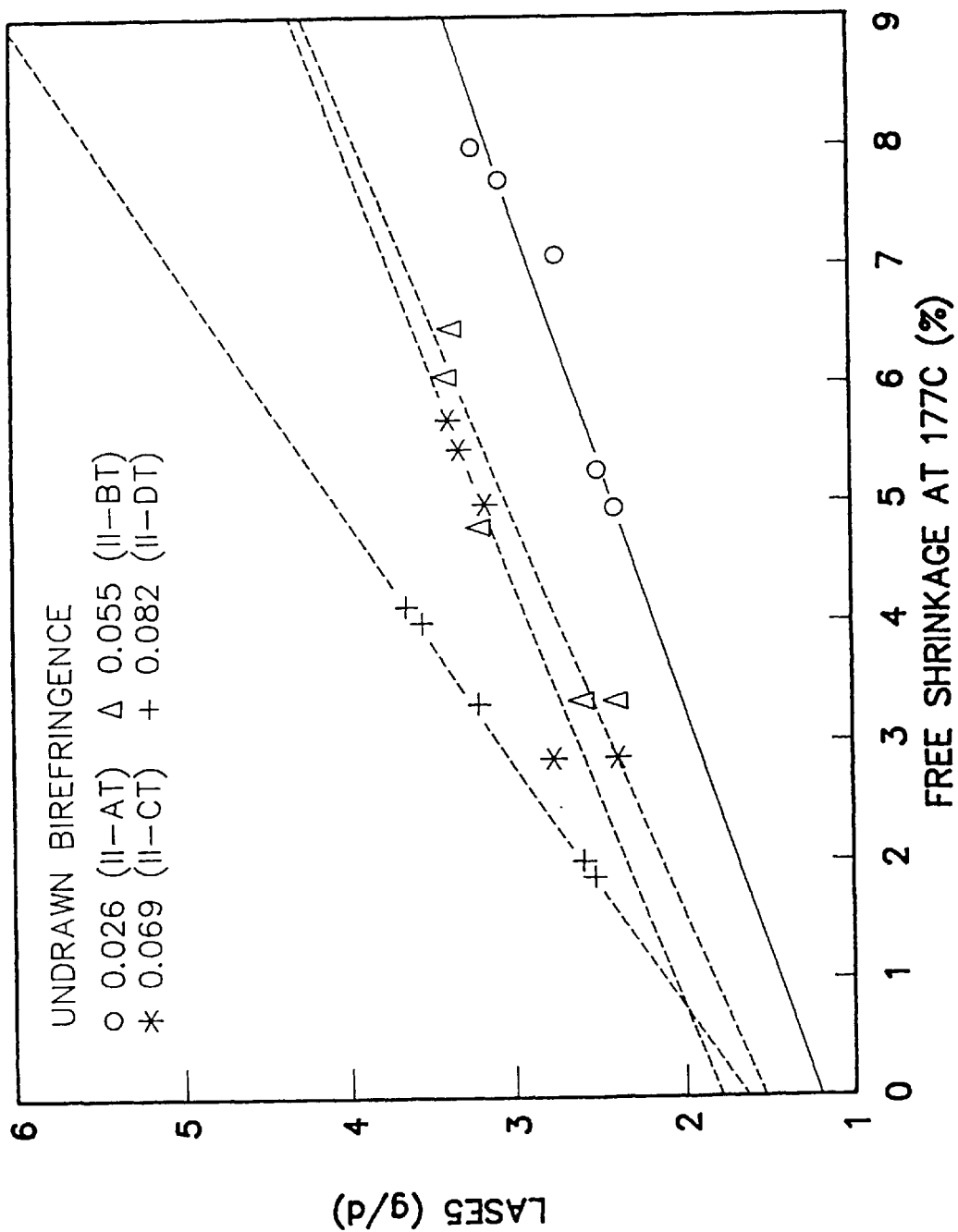
FIG. 3 represents treated cord dimensional stability as judged by plots of LASE-5 versus free shrinkage for the yarns prepared in Example II.

The high strength polyester multifilament yarn of the present invention provides improved dimensional stability together with improved treated cord tenacity when incorporated as fibrous reinforcement into rubber composites such as tires.

With the current emphasis on the monoply radial passenger tire, the demand for ever increasing dimensionally stable cords continues to be high. Dimensional stability is defined as high modulus at a given shrinkage and directly relates to tire sidewall indentations (SWI) and tire handling. awhile the modulus of the cord in the tire is the primary variable governing both SWI and handling, shrinkage is important in two ways. First, excessive cord shrinkage during tire curing can significantly reduce the modulus from that of the starting treated cord. Second, cord shrinkage is a potential source of tire non-uniformity. Thus, comparison of modulus and tenacity at a given shrinkage is a meaningful comparison for tire cords. Since tire cords experience deformations of a few percent during service, a good practical measure of modulus is LASE-5 (load at 5 percent elongation). Alternatively, $E_{4.5}$ (elongation at 4.5 g/d load) can be used as a practical measure of compliance.

For both tire SWI and handling, modulus at elevated temperature (up to 120° C.) is the 'true' parameter governing performance. Due to the highly crystalline nature of treated cords based on conventional or dimensionally stable yarns, the modulus retention (in percent) at elevated tire temperatures is essentially similar for all current commercial treated cords and for those of this invention. Thus, room temperature measurement of LASE-5 is sufficient to establish meaningful differences in cord dimensional stability.

The polyester yarn contains at least 90 mol percent polyethylene terephthalate (PET). In a preferred embodiment, the polyester is substantially all polyethylene terephthalate. Alternatively, the polyester may incorporate as copolymer units minor amounts of units derived from one or more ester-forming ingredients other than ethylene glycol and terephthalic acid or its derivatives. Illustrative examples of other ester-forming ingredients which may be copolymerized with the polyethylene terephthalate units include glycols such as diethylene glycol, trimethylene glycol, tetramethylene glycol, hexamethylene glycol, etc., and dicarboxylic acids such as isophthalic acid, hexahydroterephthalic acid, bibenzoic acid, adipic acid, sebacic acid, azelaic acid, etc.

The multifilament yarn of the present invention commonly possesses a denier per filament of about 1 to 20 (e.g. about 3 to 10), and commonly consists of about 6 to 600 continuous filaments (e.g. about 20 to 400 continuous filaments). The denier per filament and the number of continuous filaments present in the yarn may be varied widely as will be apparent to those skilled in the art.

The multifilament yarn is particularly suited for use in industrial applications wherein high strength polyester fibers have been utilized in the prior art. The yarn of this invention is particularly suitable for use as tire cord for the reinforcement of tires and for the fiber reinforcement of rubber articles and other composite structures. The fibers are particularly suited for use in environments where elevated temperatures (e.g. 80° C. to 180° C.) are encountered. Not only does the filamentary material undergo a relatively low degree of shrinkage for a high strength fibrous material, but it provides enhanced translational efficiency for tenacity when the yarn is translated into treated cord.

The unexpected combination of tenacity and dimensional stability seems to originate from the emergence of a two-phase structure (crystal plus amorphous) during spinning. As a threshold amorphous orientation is achieved there is a simultaneous crystallization of the more oriented amorphous regions.

In the conventional PET yarn process, crystallization occurs mainly in the drawing step since orientation in the spinning column is low. In current commercial dimensionally stable yarn processes, there is significant amorphous orientation during spinning but crystallization essentially occurs only in the drawing step. In the present invention, the amorphous orientation in spinning is sufficient to result in modest levels of oriented crystalline nuclei (with a degree of 3 to 15 percent). The consequence of this crystalline nucleation is to remove the high end of amorphous-orientation distribution leaving behind the less oriented amorphous regions. Thus, while the overall orientation increases with increased spinning stress, the amorphous orientation decreases immediately following the onset of crystallization in the spin-line. Further increasing the spin-line stress results in more net orientation and more separation of the more oriented amorphous regions via crystallization. The net result is further increased amorphous orientation at very high spinning stresses. In such a process amorphous orientation first increases with spinning stress prior to threshold values where crystallization occurs, then decreases as modest spun crystallinity is achieved, and finally again increases at very high stress levels. The theoretical analysis of the consequence of crystallization on amorphous-orientation distribution has been discussed by Desai and Abhiraman [J. Polym. Sci., Polym. Letters Edition, 23, 213–217 (1985)].

The characterization parameters referred to herein may conveniently be determined by testing the multifilament yarn which consists of substantially parallel filaments.

Birefringence was determined using a polarizing light microscope equipped with a Berek compensator and the fraction crystallinity was determined by conventional density measurements. The amorphous orientation function was determined from the following relationship (see R. J. Samuels, Structured Polymer Properties, New York, John Wiley & Sons).

$$\Delta n = X f_c \Delta n_c + (1-X) f_a \Delta n_a + \Delta n_f$$

where
$\Delta n$=birefringence
$x$=fraction crystalline
$f_c$=crystalline orientation function
$\Delta n_c$=intrinsic birefringence of crystal (0.220 for polyethylene terephthalate)
$f_a$=amorphous orientation function
$\Delta n_a$=intrinsic birefringence of amorphous (0.275 for polyethylene terephthalate)
$\Delta n_f$=form birefringence (negligable for this system)

Crystal orientations were determined with Herman's orientation function employing the average angular azimuthal breadth of the (010) and (100) reflections of the wide angle x-ray diffraction pattern:

$$f_c = \frac{1}{2}(3 \cos^2 \phi - 1)$$

where,
$f_c$=crystal orientation function
$\phi$=average orientation angle

Density of the undrawn and drawn yarn is a convenient measure of percent crystallinity. Densities of undrawn and drawn yarns were determined in n-heptane/carbon tetrachloride density gradient column at 23° C. The gradient column was prepared and calibrated according to ASTM D1505-68 with density ranging from 1.30–1.43 g/cm$^3$. Percent crystallinity was then calculated from $$XTAL \% = \frac{(\rho_s - \rho_a)}{(\rho_c - \rho_a)} \times 100$$

$\rho s$—measured density of sample in gm/cm$^3$
$\rho a$—theoretical density of 100% amorphous phase (1.335 gm/cm$^3$)
$\rho c$—theoretical density of 100% crystalline phase (1.529 gm/cm$^3$)

While birefringence and crystallinity measurements are effective for characterizing the amorphous orientation of drawn yarns, undrawn yarn produced near the transition between oriented-amorphous and oriented-crystalline structures demands a more direct method of evaluating degree of orientation in the amorphous phase. For this, wide angle X-Ray diffraction patterns were obtained in the transmission geometry on a Philips diffractometer with Cu radiation and diffracted beam monochromator. Several radial scans were obtained at various azimuthal angles between the equator and the meridian. These scans were resolved into crystalline and amorphous components through a DuPont curve resolver (Gaussian lineshape). The azimuthal half-width at half-height ($\phi\frac{1}{2}$) for the intensity distribution of amorphous halo was determined by plotting the height of amorphous peak as a function of azimuthal angle.

Melting points (M.P.) were determined with a Perkin-Elmer Differential Scanning Calorimeter (DSC) from the maxima of the endotherm resulting from scanning a 2 mg sample at 20° C. per minute. As shown in FIG. 9, M.P. is taken to be the temperature of she highest temperature peak of the DSC trace. Melting point elevations cited are defined as the difference between the specimen melting point (M.P.) and the meltingpoint (M.P.Q.) of a specimen after subsequent rapid liquid nitrogen quenching of an encapsulated DSC sample from the mnelt. The melting point of this re-crystallized sample is due to crystals which have cold-crystallized during the melting point test procedure. An alternate measure of melting point characteristic (Z) which is a more sensitive parameter than M.P. for many samples of this invention, is defined as the height ($H_9$) of the trace at M.P.Q.+9° C. divided by the sum of the heights at M.P.Q.+4° C. ($H_4$) and at M.P.Q+19° C. ($H_{19}$):

$$Z = \frac{H_9}{H_4 + H_{19}}$$

The Z parameter is an important characteristic for drawn yarns which have not received a significant thermal treatment. Such drawn yarns have a per cent crystallinity from density measurements of 28% or less. Application of an effective heat treatment to the yarn results in an increase in the measured Z value and crystallinity. However, this additional heat treatment does not significantly influence the ultimate properties of the final treated cord. Thus, the measured Z value can be higher than an intrinsic value Z* which reflects inherent differences in the subsequently treated cords. This intrinsic Z* can be estimated from the measured Z and density for drawn yarns receiving a thermal treatment by the following empirical relation:

$$\log Z/Z^* = 0.033 \ (XTAL\% - 27.2)^2$$

No correction is made for yarns with 27.2% or less crystallinity. Thus, a drawn yarn with Z=1.8 and crystallinity of 29.5% would have Z*=1.3, which would be the value of Z if the measurement were made prior to the thermal treatment step. Drawn yarns of the present invention have been found to have Z* greater than or equal to 1.3. Effective heat treatment of such yarns. have produced dimensionally stable yarns with Z greater than or equal to 1.7.

Regardless of which melting point characteristic is used, the differences in thermal response provide a direct quantitative measure of differences in internal morphological structure. It is felt that this unique morphological structure rather than melting point 20 elevation per se gives rise to the desired improved performance.

Intrinsic viscosity (IV) of the polymer and yarn is a convenient measure of the degree of polymerization and molecular weight. IV is determined by measurement of relative solution viscosity ($\eta_r$) of PET sample in a mixture of phenol and tetrachloroethane (60/40 by weight) solvents. The relative solution viscosity ($\eta_r$) is the ratio of the flow time of a PET/solvent solution to the flow time of pure solvent through a standard capillary. Billmeyer approximation (J. Polym. Sci. 4, 83–86 (1949)) is used to calculate IV according to $$IV = 1/4 \frac{(\eta_r - 1)}{C} + 3/4 \frac{\ln \eta_r}{C}$$

where C is concentration in gm/100 ml.

The tenacity values (i.e. at least 7 grams per denier), compare favorably with these particular parameters exhibited by commercially available polyethylene terephthalate tire cord yarns. The tensile properties referred to herein were determined on yarns conditioned for two hours through the utilization of an Instron tensile tester (Model TM) using a 10-inch gauge length and a strain rate of 120 percent per minute in accordance with ASTM D885. All tensile measurements were made at room temperature.

The high strength multifilament yarn of the present invention possesses an internal morphology which, for a LASE-5 of 4.5 grams per denier or greater, manifests an unusually low free shrinkage propensity of less than 8 percent, and preferably less than 6 percent when measured in air at 177° C. For instance, filaments of commercially available dimensionally stable tire cord yarns based on polyethylene terephthalate commonly shrink about 6 to 10 percent when tested in air at 177° C. Free shrinkage (FS) values were determined in accordance with ASTM D 885 with the exception that the testing load was 9.3 grams. Such improved dimensional stability is of particular importance if the product serves as fibrous reinforcement in a radial tire. Elongation at the specified load of 4.5 g/d ($E_{4.5}$) is an alternate indicator of modulus. It is particularly useful in that the sum $E_{4.5}$+FS :is a good indicator of dimensional stability for yarns processed under different relaxation levels. Lower sums ($E_{4.5}$+FS) indicate better dimensional stability.

The Kinetic Theory of Rubber Elasticity allows computation of an effective number of crosslinks in a yarn. These crosslink values are imagined to be a measure of the ability of the crystals to tie together the amorphous regions, either via tie chains or crystal proximity. The relationship of interest is:

$$\sigma = NkT(A^2 - 1/A)$$

where,
 $\sigma$=shrinkage force
 k=Boltzman constant
 T=temperature
 A=extension ratio=1/(1−shrinkage)
 N=network chains or crosslinks/cc The classical method for determining crosslink density is to measure shrinkage force and shrinkage for samples which have been drawn (or relaxed) to different extents. For simplicity, we have developed a method which allows one to determine analogous data by measuring the shrinkage at a variety of constraining forces. For this modified technique, the constraining force corresponds to the shrinkage force. The shrinkage value needed for the effective crosslink calculation is the difference between the shrinkage measured at a given constraining force and the shrinkage measured at a minimal constraining force of 5 grams. Note that since curvature is exhibited at high shrinkage forces only data up to a shrinkage force of 0.08 g/d should be used for the above computation. For industrial applications, a temperature of 177° C. was employed.

Identified hereafter is a description of a process which has been found to be capable of forming the improved yarn of the present invention. The yarn product claimed hereafter is not to be limited by the parameters of the process which follows.

The melt-spinnable polyester is supplied to an extrusion spinnerette at a temperature above its melting point and below the temperature at which the polymer degrades substantially. The residence time at this stage is kept to a minimum and the temperature should not rise above 315° C., preferably 310° C. The flow curve of molten PET in terms of melt viscosity versus shear rate has been shown to be important for steady-state melt spinning giving uniform individual multifilaments. For a circular spinnerette hole where flow is steady and end-effects are negligible, the apparent shear rate ($\dot{\gamma}$) at the wall of the capillary is given by $$\dot{\gamma} = \frac{4Q}{\pi R^3}$$

where
Q=flow rate through the capillary in m³/sec (calculate using mete density of 1.30 g/cc)
R=radius of the capillary in meters.

The extruded filaments then traverse a conventional yarn solidification zone where quench air impinges on the spun yarn thereby freezing in desirable internal structural features and preventing the filaments from fusing to one another. The solidification zone comprises (a) a retarded cooling zone, preferably comprising a gaseous atmosphere heated at a temperature of 150 to 450° C., and (b) a cooling zone adjacent said retarded cooling zone wherein said yarn is rapidly cooled and solidified in a blown air atmosphere. The key to the current process is to utilize extruding polymer with IV greater than 0.80 and adjust processing conditions to achieve a crystalline, partially oriented yarn with a crystallinity of 3 to 15 percent and a melting point elevation of 2 to 10° C. One skilled in the art can achieve this by adjusting the following conditions: length and temperature of an annealing zone adjacent to the spinnerette, diameter of the spinnerette holes, method of blowing the quench, quench air velocity, and drawdown in the quench column. The speed of withdrawal of the yarn from the solidification zone is as important parameter affecting the stress on the spun fiber, and should be adjusted to yield the desired characteristics. It is preferred that the melting point elevation be 2 to 5° C. and that $\phi^{1/2}$ is at least 26°.

The spun yarn was then drawn between rolls at temperatures above the glass transition temperature (80° C.) to within 85 percent of the maximum draw ratio. This drawing process involves multiple drawing and conditioning steps to achieve a tenacity above 7 grams per denier, a LASE-5 above 3.7 grams per denier and a shrinkage less than 8 percent. It is preferred that the effective crosslink density (N) be between $10 \times 10^{21}$ and $20 \times 10^{21}$ crosslinks per cubic centimeter.

It will be appreciated by those of skill in the art that the high viscosity polymer spun as above can be drawn in known ways such as that disclosed in U.S. Pat. No. 4,195,052 to Davis et al. and in U.S. Pat. No. 4,251,481 to Hamlyn. The yarn can be drawn off-line. However, for economic reasons it is preferred to draw the yarn in a continuous integrated spin-draw process.

The drawn yarns are usually twisted into a cord and then dipped into one or more conventional adhesive coatings, referred to as cord dips and then subjected to various stretch/relax sequences at elevated temperature to 5 achieve the optimum combination of tenacity, shrinkage, LASE-5. Again this technology is well-known to those skilled in the art who adjust twist and treating conditions for specific end-uses. Details for the treating conditions employed are given in the examples.

In evaluating the potential of tire yarns as treated cords, one may use a "standard" twist and cord treatment for comparative purposes. In this "standard" procedure, 1000 denier yarns are twisted to 8 turns per inch and then three ply cords are prepared again using 8 turns per inch. The cords are then dipped in an aqueous blocked diisocyanate (6% solids) just prior to passage-through a hot air oven at 440° F. for 40 seconds where the cord was stretched 6% or 8%. The emerging cord then passes through an RFL dip (20% solids) and finally through a second oven at 440° F. for 60 seconds where the cord was relaxed to varying degrees to cover the range where 4% free shrinkage is achieved. For less dimensionally stable cord controls, some extrapolation to 4% shrinkage may be necessary. The cord is wound on a bobbin for further testing. A single-end Litzler Computreater was used.

Treated cords prepared in such manner from the yarn of this invention have been shown to have the following treated cord properties:
(a) a dimensional stability defined by LASE-5 of at least 2.3 grams per denier at 4 percent free shrinkage, and
(b) a tenacity of at least 7.0 grams per denier at 4 percent free shrinkage (preferred at least 7.4 grams per denier), said dimensional stability and said tenacity being determined by interpolation of LASE-5 versus free shrinkage data to 4 percent free shrinkage.

Graphs of LASE-5 and tenacity versus free shrinkage were constructed as shown in FIGS. 1–4. Comparison between different starting yarns can be made at the interpolated values at 4% free shrinkage.

EXAMPLE I

A 1000 denier PET yarn was produced by extruding 300 individual filaments at 62.5 lbs/hr into a heated sleeve (220–300° C. Temp) and then solidifying in an air quenching column. Yarns were then taken-up at varying winder speeds. The residence times in the heated sleeve and quench columns were 0.02 to 0.03 and 0.2 seconds, respectively. The Godet speed at the bottom of the spinning column and the winder speed were adjusted to give, different undrawn birefringences and crystallinity levels. In all cases the same shear rate in the spinnerette holes was employed. Yarn intrinsic viscosity was 0.88.

These undrawn yarns were then drawn in three stages on a draw-winder. The first three godet rolls had temperatures of 120, 120, and 230° C. the last godet was ambient. The residence times were 0.7, 0.6–0.7, 0.3–0.6, and, 0.2–0.4 seconds. Yarn draw ratios and specific properties are given in Tables I and II.

The above drawn yarns were then twisted into 1000/3, 8.5×8.5 tpi cords and two-zone treated at 440° F. (227° C.) and 440° F. (227° C.) for 40 and 60 seconds. Aqueous blocked diisocyanate and RFL dips were applied prior to the two hot zones, respectively. The treated cords were prepared using +6% stretch in the first zone and various relaxations (−4, −2, and 0%) in the second zone. A stretching sequence of +8, 0% was also used. The properties of these cords are given in Table III. Treated cord dimensional stabilities, as judged by plots of LASE-5 versus free shrink (FIG. 1), increase with increasing undrawn yarn birefringence, melting point, and crystallinity.

Figure 8:
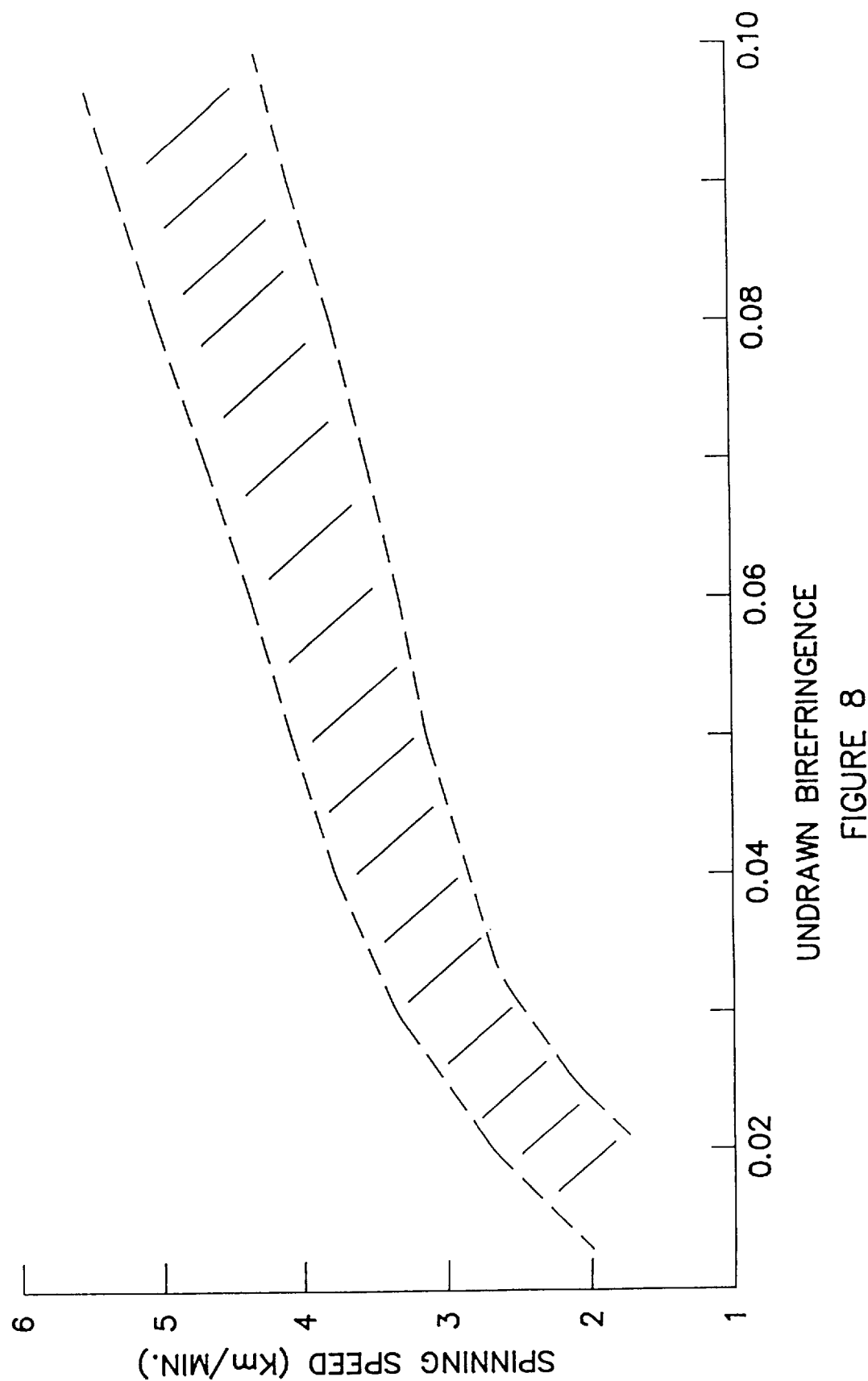
FIG. 8 gives the range of spinning speeds wherein prior art U.S. Pat. No. 4,491,657 teaches that different undrawn birefringences can be achieved.
Figure 9B:
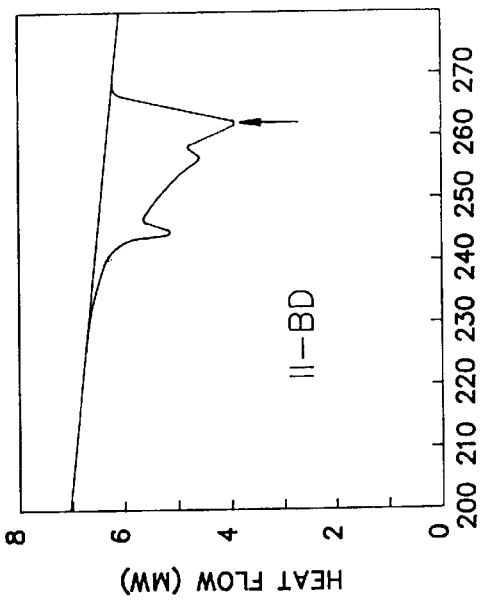
FIG. 9 gives the DSC traces for drawn yarns from Example. II.
Figure 9C:
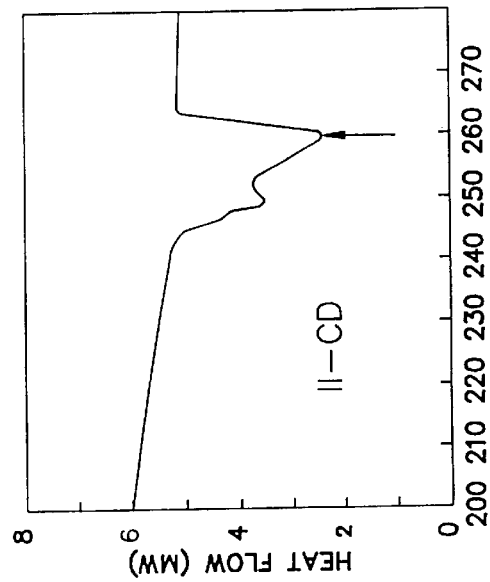
Figure 9A:
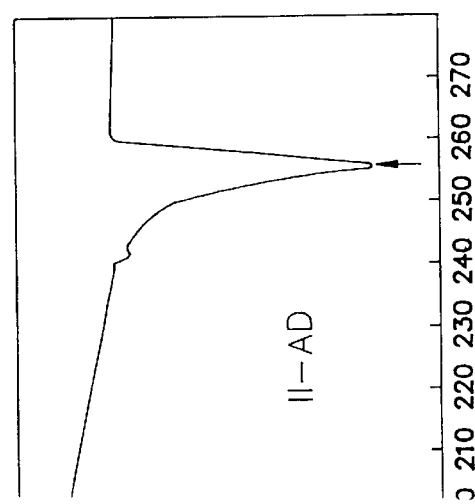
Figure 9E:
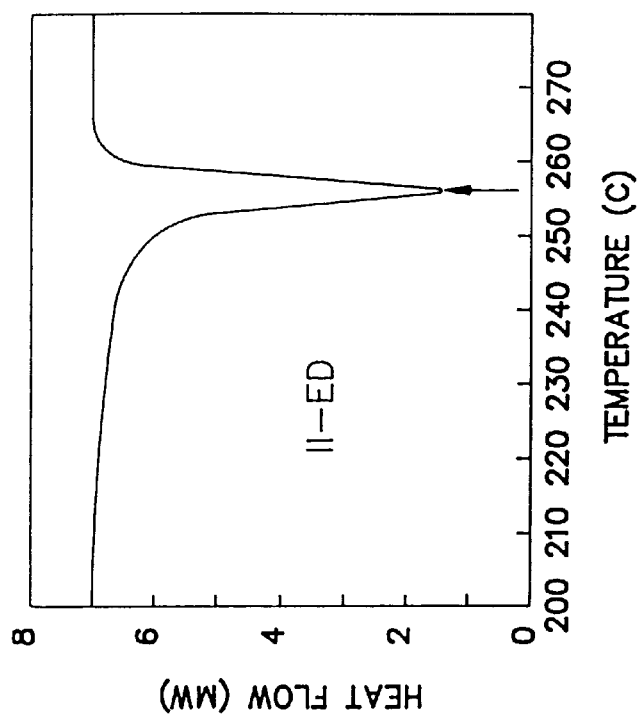
Figure 9D:
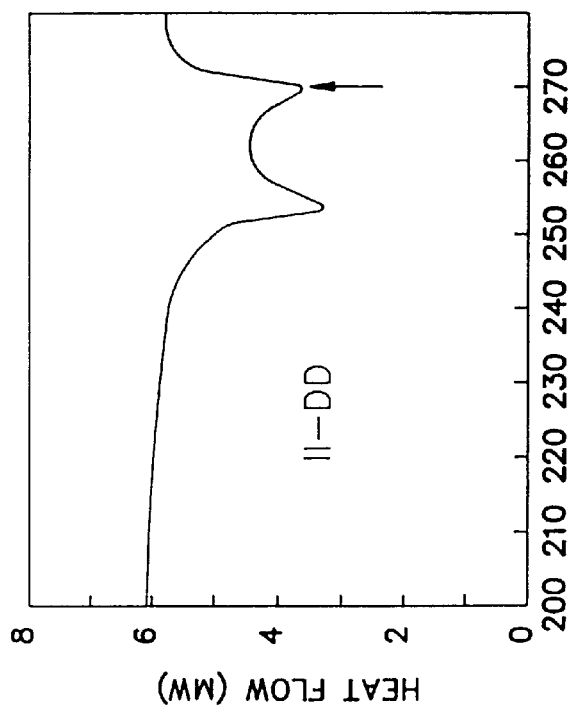

Comparison of the treated cord tenacities at a given free shrinkage (FIG. 2) clearly indicates an unexpected high tenacity for the undrawn intermediate birefringence of 0.056. This higher treated cord tenacity is equal to that for standard tire yarn processed at very low undrawn birefringence. While drawn yarn tenacities alone are not necessarily a good barometer for treated cord tenacity, the combination of yarn tenacity and dimensional stability ($E_{4.5}$+FS) does give a good indication, provided similar thermal histories are experienced during drawing. For the samples representing this invention (I-BD and I-CD), $E_{4.5}$+FS is 10.2% and 10.1% respectively, indicating highly dimensionally stable yarns. These sums would have been slightly higher (2–3%) if the yarn 10 was drawn at higher speeds where residence times on heated rolls were lower. Note the melting points (258° C. and 259° C.) lies between that for comparative examples I-AD and I-DD. Note that the spinning speed required to achieve the 0.056 undrawn birefringence is less than that for tie prior art in FIG. 8.

The yarns of this invention, I-BD and -CD, have. high measured values of Z. Their cord dimensional stabilities are similar as are their calculated Z* values, which take differences in crystallinities into account.

EXAMPLE II

Figure 7:
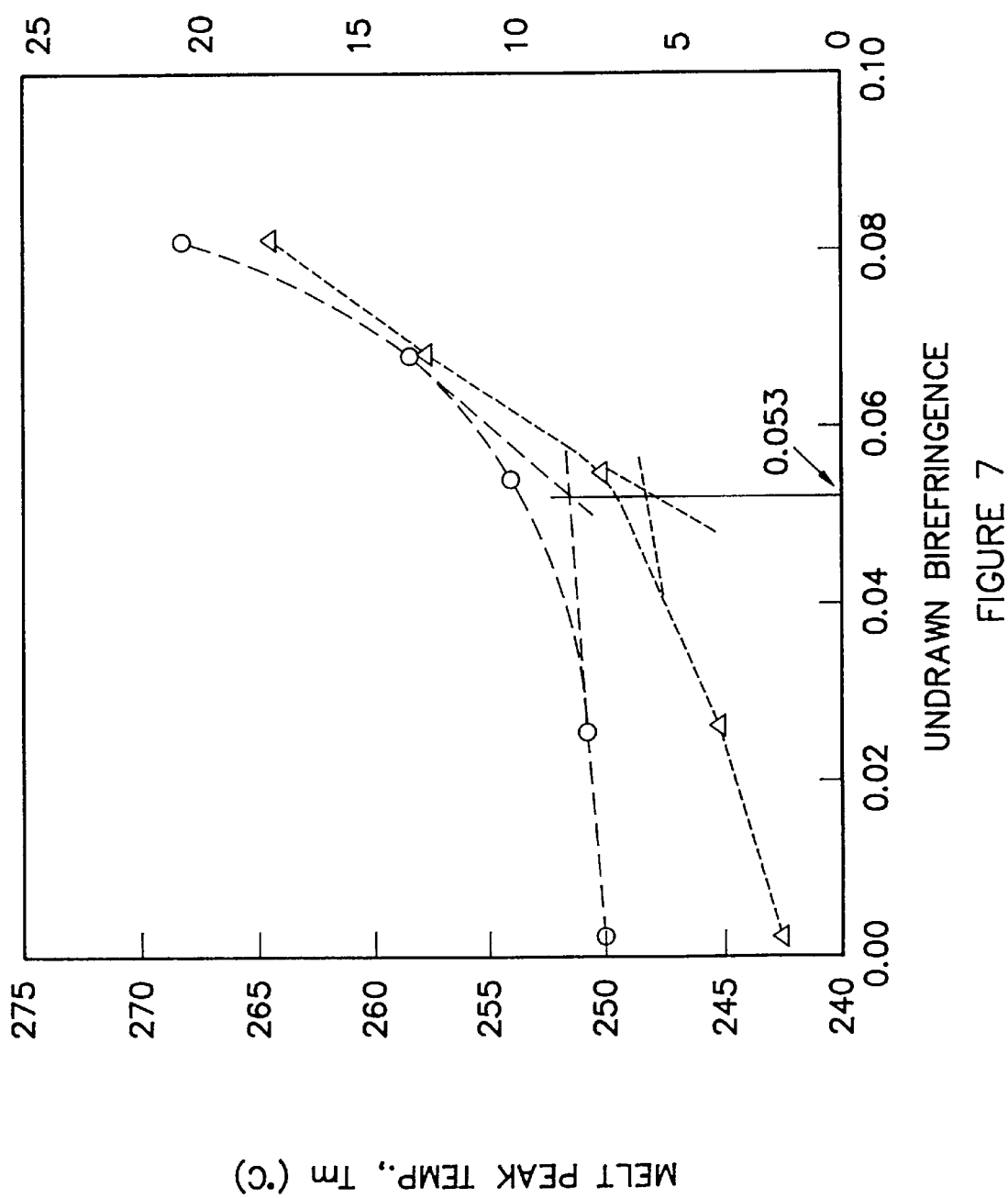
FIG. 7 represents the percent crystallinity and melting point elevation for the undrawn yarns for Example II.
Figure 10:
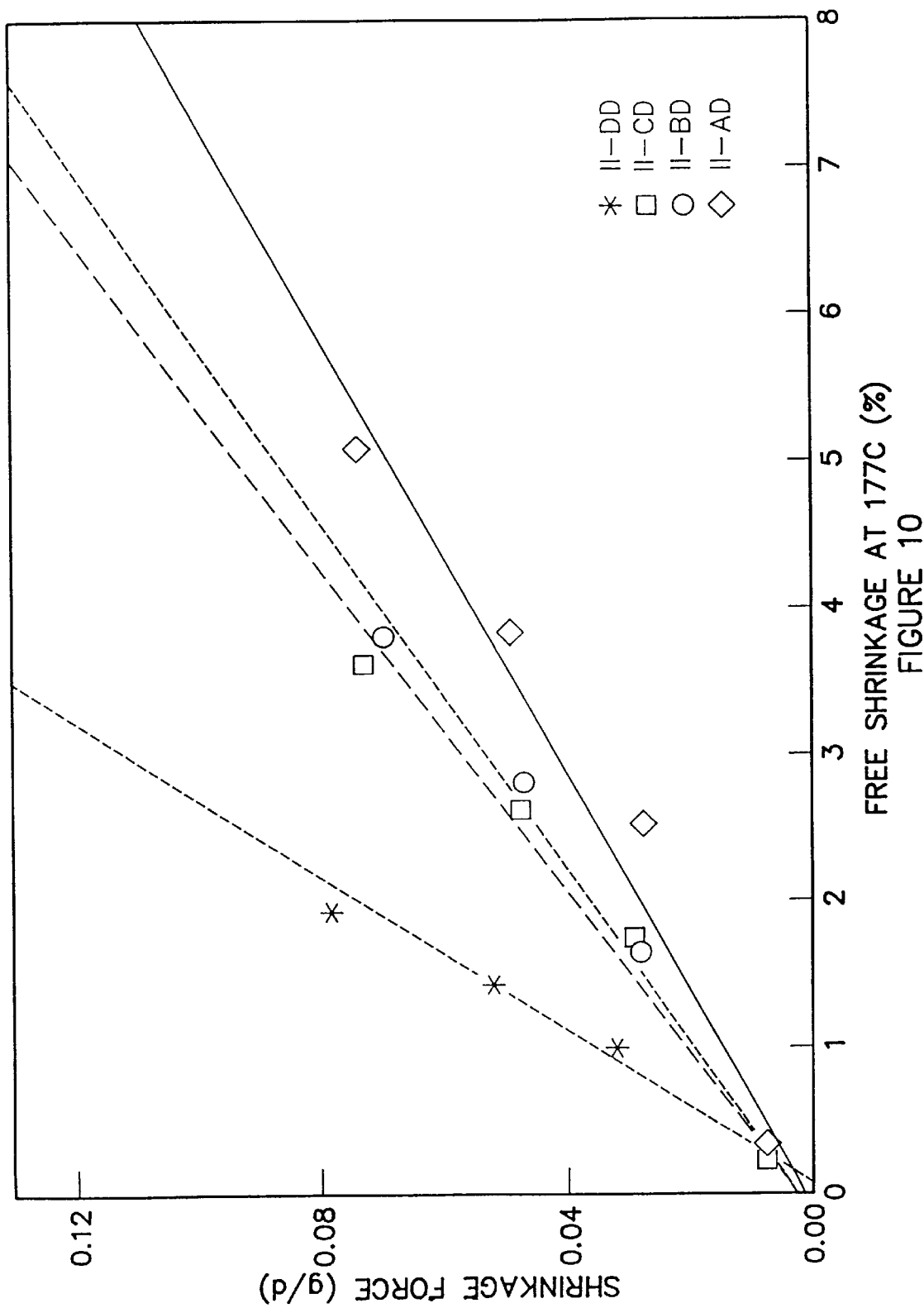
FIG. 10 represents a plot of the shrinkage force vs. free shrinkage of drawn yarns from Example II.

A higher viscosity yarn (IV=0.92) was spun under similar conditions as in Example I except that several spinnerette shear rates were used. Following the same procedure as in Example I, the winder speed was adjusted to provide different undrawn crystallinities. This undrawn yarn was continuously transported to the panel draw rolls. Details for the undrawn and drawn yarns are given in Tables IV and V. The residence times on the draw rolls was 0.05 to 0.1 second and the godet temperatures were 90° C., ambient, 220° C., and 150° C. For comparison, values for a conventional yarn spin to 0.002 undrawn birefringence are also given. From FIG. 7 it is readily seen that the products of this invention (II-B and II-C) are prepared in the transition region where significant crystallinity 30 occurs in the spinline. The effective number of crosslinks in Table V is calculated from the shrinkage versus shrink force curves in FIG. 10.

Figure 4:
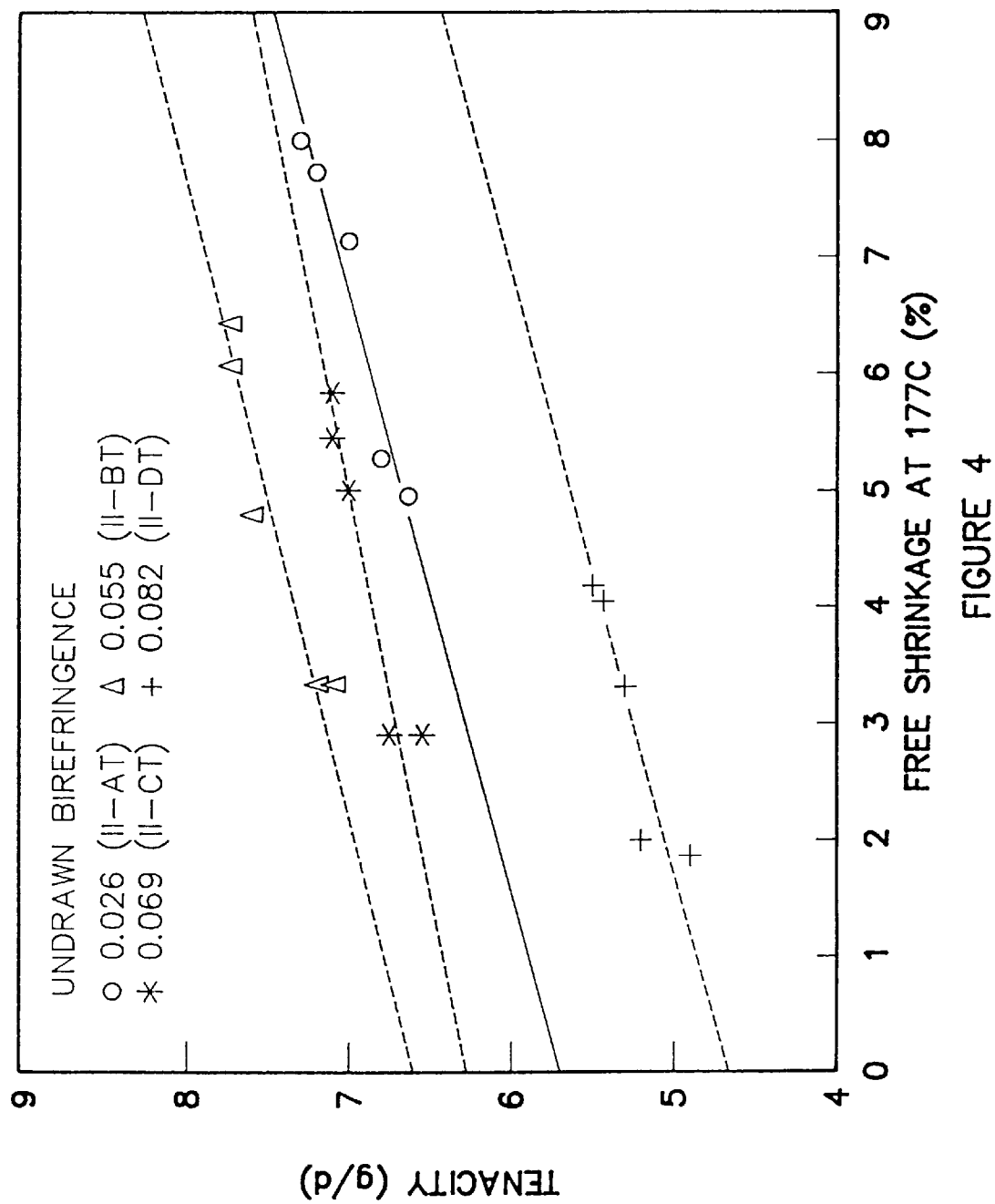
FIG. 4 represents a comparison of treated cord tenacities at a given free shrinkage for the yarns of Example II.

The preceeding drawn yarns were twisted into a 1000/3, 8×8 tpi cord and then treated per Example I. Again 35 treated cord dimensional stability (Table VI and FIG. 3) increased with undrawn crystallinity. However as shown in FIG. 4, the highest tenacity was achieved at intermediate LASE-5. The corresponding drawn yarns have tenacity greater than 7.3 g/d, $E_{4.5}$+FS less than 12.9%, intermediate melting points (259 and 262° C.), low amorphous orientation, and a melting trace intensity parameter (Z*) of at least 1.3. The actual DSC traces are given in FIG. 9. when slight differences in twist are taken into account, the dimensional stability of II-BD is similar to I-BD and -CD. The measured Z is much lower than those for Example I, which have higher crystallinity due to lower viscosity and slower drawing stages. Due to the high drawing speeds and modest roll temperatures, none of the samples in this example received an effective heat treatment. The maximum crystallinity without heat treatment is 27–28% with 27.2% representing the average.

Figure 5:
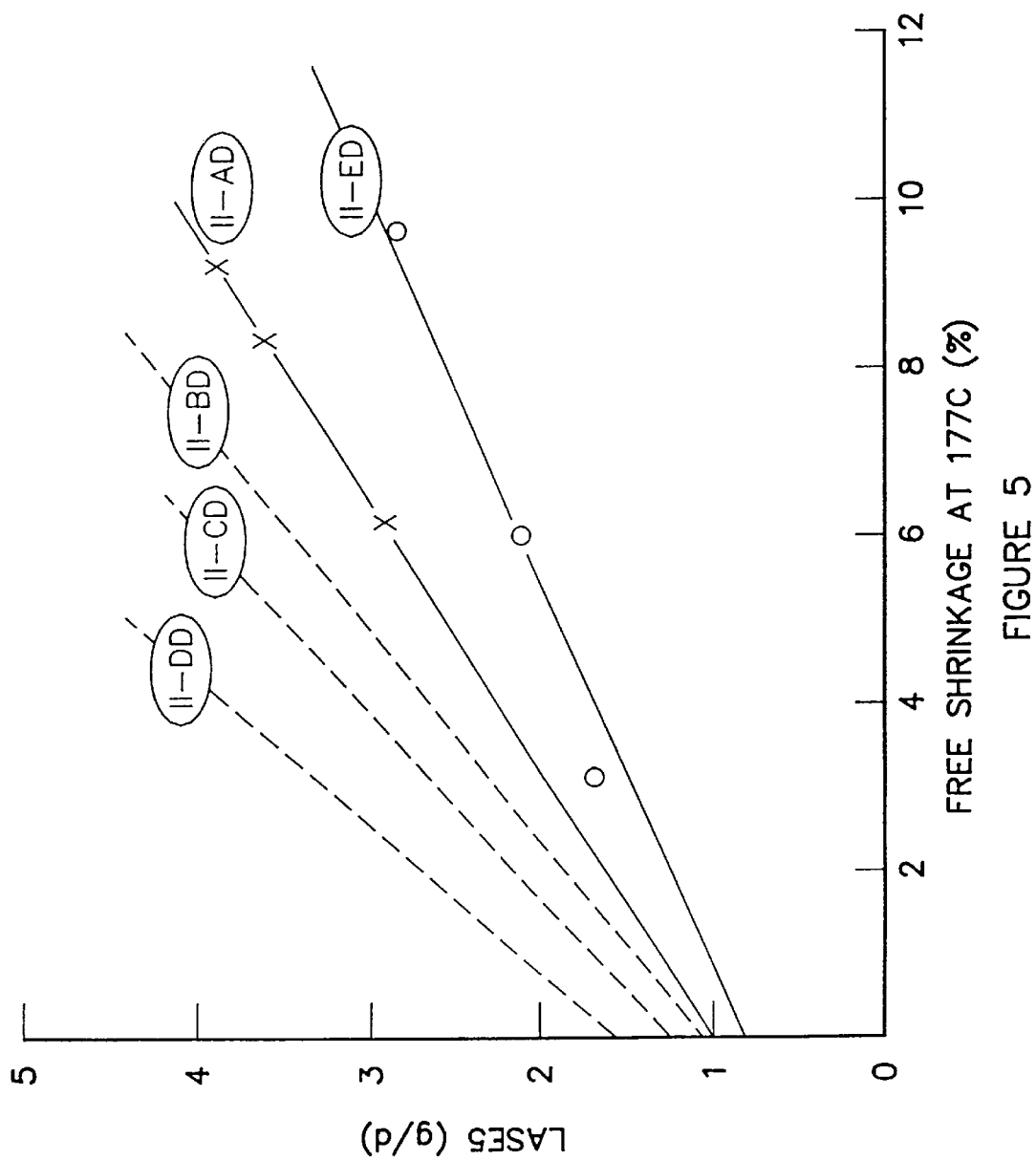
FIG. 5 represents a plot of LASE-5 versus free shrinkage of drawn yarns from Example II.

LASE-5 versus free shrink can be used as an alternate measure of drawn yarn dimensional stability. FIG. 5 gives such a plot for drawn yarns prepared similar to II-AD and II-ED, but then relaxed to various degrees in the final zone. The solid lines in FIG. 5 represent the data for the relaxation series where (x) and (o) represent points for yarns similar to II-AD and II-ED, respectively. The individual data points from Table IV are also plotted as encircled sample designations from Table IV. One would expect a family of linear lines with increasing slope. On this basis, the products of this invention would be defined by LASE-5 (g/d)>0.35[Free Shrink (%)]+1.0.

Figure 6:
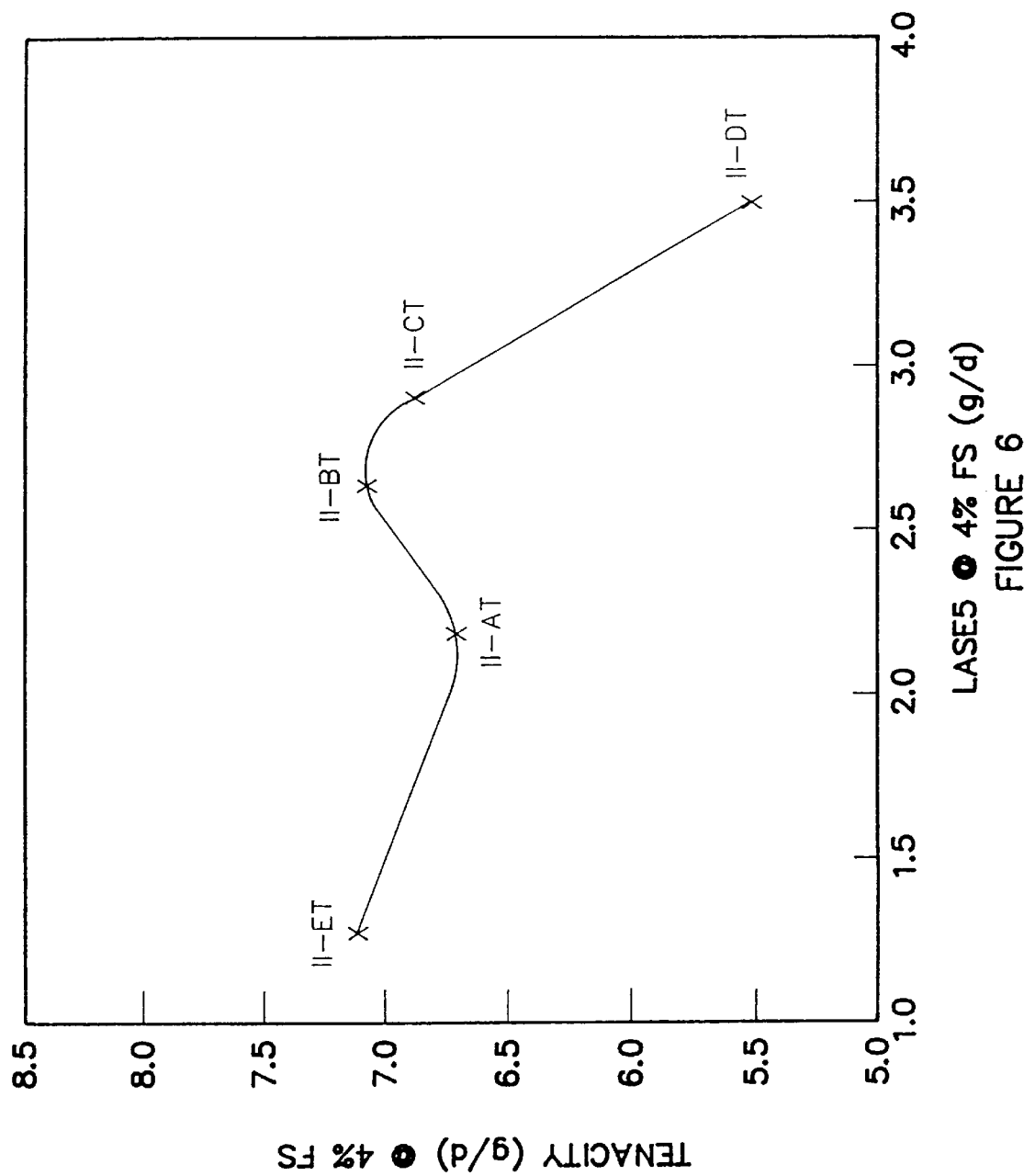
FIG. 6 plots treated cord tenacity versus LASE-5 at a given free shrinkage (4 percent) and demonstrates the unexpected increase in treated cord tenacity obtained by the yarns of this invention. (Example II).

The advantages of this patent are more clearly shown by FIG. 6 which plots tenacity versus LASE-5 at a given free shrinkage (4%). Based on the decrease in tenacity in-going from conventional yarn (undrawn $\Delta N$=0.002) to prior art DSP's (undrawn $\Delta N$=0.026), one would expect the continual decrease in treated cord tenacity with increasing LASE-5, particularly in light of the low tenacity at very high undrawn $\Delta N$=0.082). Instead one sees an unexpected maximum at intermediate LASE-5. Again note that the spinning speeds required are much less than those taught in U.S. Pat. No. 4,491,657. This lower speed allows preparation of fibers in a continuous spin-draw process without the need for expensive high speed equipment.

EXAMPLE III

This example shows that yarn tenacity and dimensional stability Ore not sufficient criteria to define the product of this invention. Yarns spun to 0.002 and 0.026 undrawn birefringences were then drawn in the manner described in Example II. They were then given heat treatments of either (a) 6 seconds @ 245° C. or (b) several hours @ 210° C. at constant length. Subsequently, the yarn was corded (1000/3, 8.5×8.5) and treated per Example I. The data in Table VII shows that additional parameters of melting point elevations and amorphous orientations are necessary to specify yarns of this invention. The lower amorphous orientation yarns of this invention are expected to have longer flex-life.

EXAMPLE IV

This example shows that one must focus on fundamental properties such as undrawn yarn crystallinity and melting point elevation and not on undrawn birefringence alone. A yarn series was processed under similar conditions to Example I, only the thruput was 75 lbs/hr, the heated sleeve was 400° C., and the spinnerette shear rate was 766 sec$^{-1}$. At 0.058 undrawn birefringence, the drawn yarn tenacity/UE/LASE-5/FS/$E_{4.5}$+FS was 8.1/9.9/4.1/8.6/14.8. At 0.081 undrawn birefringence, the drawn yarn was 8.0/9.5/4.1/7.5/11.9. The two drawn yarns had melting point elevations of 8 and 13° C., respectively. Under the standard treating conditions, the tenacity and LASE-5 values at 4% FS were 6.7 g/d and 2.2 g/d for the 0.058 undrawn birefringence compared to 7.1 g/d and 2.6 g/d for the 0.081 undrawn birefringence yarn. Only the latter product was within the scope of this invention even though the undrawn birefringence for the former was similar to that for I-BD and I-CD, which are within the scope of this invention.

TABLE I

UNDRAWN YARN (IV = 0.88)

| Example | Spinning Speed m/min | Spinnerette Shear Rate, Sec$^{-1}$ | $\Delta N$ | M.P., ° C. | $\Delta$M.P. |
|---|---|---|---|---|---|
| I-A | 1760 | 2150 | 0.028 | 250 | 1 |
| I-B,I-C | 2900 | 2150 | 0.056 | 252 | 3 |
| I-D | 3500 | 2150 | 0.088 | 261 | 12 |

| Example | Density, g/cm$^3$ | XTAL, % |
|---|---|---|
| I-A | 1.3385 | 2 |
| I-B,I-C | 1.3480 | 4 |
| I-D | 1.3701 | 18 |

TABLE IV

UNDRAWN YARN (IV = 0.92)

| Example | Spinning Speed m/min | Spinnerette Shear Rate, Sec$^{-1}$ | ΔN | M.P., °C. | Δm.p. |
|---|---|---|---|---|---|
| II-A | 1760 | 2150 | 0.026 | 249 | 0 |
| II-B | 2020 | 910 | 0.055 | 252 | 3 |
| II-C | 2420 | 980 | 0.069 | 253 | 4 |
| II-D | 2990 | 640 | 0.082 | 265 | 16 |
| II-E | 480 | 1440 | 0.002 | 249 | 0 |

| Example | Density, g/cm³ | XTAL, % | $\phi_{1/2}$ (deg) |
|---|---|---|---|
| II-A | 1.3430 | 3 | 21 |
| II-B | 1.3494 | 7 | 32 |
| II-C | 1.3603 | 13 | — |
| II-D | 1.3707 | 18 | 19 |
| II-E | 1.3385 | 2 | — |

TABLE II

DRAWN YARN (IV = 0.88)

| Example[a] | Draw Ratio 1 | Draw Ratio 2 | Draw Ratio 3 | Denier | Tenacity g/d | LASE-5 g/d | $E_{4.5}$ % |
|---|---|---|---|---|---|---|---|
| I-AD | 1.72 | 1.38 | 1.03 | 1016 | 7.8 | 4.1 | 5.2 |
| I-BD | 1.72 | 1.10 | 1.04 | 898 | 7.8 | 5.4 | 4.1 |
| I-CD | 1.72 | 1.10 | 0.98 | 943 | 7.0 | 4.0 | 4.6 |
| I-DD | 1.40 | 1.10 | 1.05 | 799 | 6.5 | 5.8 | 3.2 |

| Example[a] | Terminal Mod. g/d | UE, % | FS(%), @177° C. | $E_{4.5}$, +FS, % | M.P., °C. |
|---|---|---|---|---|---|
| I-AD | 128 | 9.8 | 9.0 | 14.2 | 257 |
| I-BD | 111 | 7.2 | 6.1 | 10.2 | 258 |
| I-CD | 54 | 8.9 | 5.5 | 10.1 | 259 |
| I-DD | 78 | 6.2 | 4.7 | 7.9 | 267 |

| Example[a] | ΔM.P.[b] | Fa | Z | Z* | XTAL% |
|---|---|---|---|---|---|
| I-AD | 8 | 0.73 | 0.4 | 0.3 | 29.3 |
| I-BD | 9 | 0.71 | 2.5 | 1.5 | 30.2 |
| I-CD | 10 | 0.70 | 1.7 | 1.4 | 29.2 |
| I-DD | 18 | 0.68 | 0.6 | 0.2 | 31.4 |

[a]I-AD signifies undrawn I-A after drawing, and so on.
[b]Melting Point for melted, quenched, and then remelted fiber was 249° C.

TABLE III

TREATED CORD PROPERTIES (IV = 0.88)

| Example[a] | Stretch | Tenacity, g/d | LASE-5, g/d | FS(%), at 177° C. | UE, % | Toughness, g/d |
|---|---|---|---|---|---|---|
| I-AT | +6/−4 | 6.0 | 2.48 | 4.8 | 11.7 | 0.34 |
| | +6/−2 | 6.0 | 2.62 | 5.4 | 11.5 | 0.34 |
| | +6/−0 | 6.0 | 3.01 | 6.7 | 10.1 | 0.30 |
| | +8/−0 | 6.0 | 2.95 | 7.0 | 9.7 | 0.29 |
| I-BT | +6/−4 | 6.6 | 2.70 | 4.2 | 13.6 | 0.50 |
| | +6/−2 | 6.7 | 3.34 | 6.3 | 11.6 | 0.44 |
| | +6/−0 | 6.7 | 3.46 | 6.7 | 10.6 | 0.38 |
| | +8/−0 | 7.0 | 3.50 | 6.8 | 11.0 | 0.42 |
| I-CT | +6/−4 | 6.3 | 2.20 | 2.6 | 16.1 | 0.59 |
| | +6/−2 | 6.3 | 2.64 | 3.7 | 14.4 | 0.53 |
| | +6/−0 | 6.5 | 2.99 | 4.6 | 13.3 | 0.50 |
| | +8/−0 | 6.4 | 3.08 | 4.8 | 13.3 | 0.51 |
| I-DT | +6/−4 | 5.8 | 3.77 | 3.3 | 10.2 | 0.36 |
| | +6/−2 | 5.6 | 3.58 | 3.2 | 11.2 | 0.39 |
| | +6/−0 | 5.6 | 3.87 | 3.9 | 10.9 | 0.39 |
| | +8/−0 | 6.0 | 4.00 | 4.1 | 9.1 | 0.31 |

[a]Undrawn I-A after drawing and treating is I-AT and so on.

TABLE V

DRAWN YARN (IV = 0.92)

| Example[a] | Draw Ratio 1 | Draw Ratio 2 | Draw Ratio 3 | Denier | Tenacity g/d | Lase-5 g/d | Terminal Modulus g/d |
|---|---|---|---|---|---|---|---|
| II-AD | 1.73 | 1.46 | 0.98 | 1008 | 8.1 | 3.9 | 95 |
| II-BD | 1.73 | 1.25 | 0.99 | 1007 | 8.1 | 4.0 | 128 |
| II-CD | 1.73 | 1.16 | 1.00 | 982 | 7.3 | 3.9 | — |
| II-DD | 1.40 | 1.15 | 1.00 | 924 | 5.8 | 4.1 | 78 |
| II-ED | — | — | — | 1005 | 9.3 | 3.1 | — |

| Example | $E_{4.5}$, % | UE, % | Free Shrink, @177° C. | $E_{4.5}$, +FS, % | M.P., °C. | ΔM.P.[b] |
|---|---|---|---|---|---|---|
| II-AD | 5.5 | 10.0 | 10.0 | 15.5 | 256 | 7 |
| II-BD | 5.5 | 9.9 | 7.4 | 12.9 | 258 | 10 |
| II-CD | 5.7 | 10.0 | 5.8 | 11.5 | 259 | 10 |
| II-DD | 6.5 | 16.5 | 4.3 | 10.8 | 269 | 20 |
| II-ED | 6.9 | 15.3 | 10.8 | 17.7 | 255 | 6 |

| Example | Z | Z* | Fa | XTAL% | N[c] |
|---|---|---|---|---|---|
| II-AD | 0.7 | 0.7 | 0.70 | 27.5 | 8.4 |
| II-BD | 1.5 | 1.5 | 0.66 | 26.6 | 11.6 |
| II-CD | 1.3 | 1.3 | 0.64 | 27.6 | — |
| II-DD | 0.3 | 0.3 | 0.58 | 28.7 | 26.6 |
| II-ED | <0.1 | — | 0.87 | — | — |

[a]II-AD signifies undrawn I-A after drawing, and so on
[b]Melting Point for melted, quenched, and remelted fiber was 249° C.
[c]10$^{21}$ crosslinks per cubic centimeter

TABLE VI

TREATED CORD PROPERTIES (IV = 0.92)

| Example | Stretch | Tenacity, g/d | LASE-5, g/d | FS(%), at 177° C. | UE, % | Toughness, g/d |
|---|---|---|---|---|---|---|
| II-AT | +1/−0 | 6.7 | 2.43 | 4.9 | 15.0 | 0.50 |
| | +6/−4 | 6.9 | 2.50 | 5.1 | 13.7 | 0.47 |
| | +6/−2 | 7.0 | 2.80 | 6.9 | 11.5 | 0.40 |
| | +6/−0 | 7.3 | 3.08 | 7.5 | 11.1 | 0.41 |
| | +8/−0 | 7.3 | 3.24 | 7.8 | 11.0 | 0.40 |
| II-BT | +1/−0 | 7.1 | 2.41 | 3.2 | 16.4 | 0.62 |
| | +6/−4 | 7.2 | 2.55 | 3.2 | 16.1 | 0.61 |
| | +6/−2 | 7.6 | 3.20 | 4.7 | 14.9 | 0.60 |
| | +6/−0 | 7.7 | 3.39 | 5.9 | 13.3 | 0.56 |
| | +8/−0 | 7.7 | 3.37 | 6.3 | 12.6 | 0.53 |
| II-CT | +1/−0 | 6.6 | 2.40 | 2.9 | 16.3 | 0.61 |
| | +6/−4 | 6.8 | 2.73 | 2.9 | 16.1 | 0.62 |
| | +6/−2 | 7.0 | 3.16 | 5.0 | 13.9 | 0.57 |
| | +6/−0 | 7.1 | 3.24 | 5.4 | 13.0 | 0.50 |
| | +8/−0 | 7.1 | 3.36 | 5.8 | 12.6 | 0.50 |
| II-DT | +1/−0 | 4.9 | 2.50 | 1.8 | 18.9 | 0.66 |
| | +6/−4 | 5.2 | 2.56 | 1.9 | 18.5 | 0.64 |
| | +6/−2 | 5.3 | 3.14 | 3.2 | 16.9 | 0.64 |
| | +6/−0 | 5.4 | 3.53 | 3.9 | 15.2 | 0.59 |

TABLE VI-continued

TREATED CORD PROPERTIES (IV = 0.92)

| Example | Stretch | Tenacity, g/d | LASE-5, g/d | FS(%), at 177° C. | UE, % | Toughness, g/d |
|---|---|---|---|---|---|---|
| II-ET | +8/−0 | 5.6 | 3.60 | 4.0 | 14.1 | 0.53 |
| | +1/−2 | 7.3 | 2.4 | 7.3 | 16.9 | 0.64 |
| | +6/−4 | 7.0 | 2.2 | 6.8 | 17.5 | 0.62 |
| | +6/−2 | 7.4 | 2.9 | 8.9 | 14.8 | 0.59 |
| | +6/−0 | 7.4 | 3.3 | 10.2 | 13.2 | 0.54 |

TABLE VII

| Undrawn Birefringence | Yarn Heat Treatment | Yarn Tenacity, g/d | $E_{4.5}$ +FS, % | M.P., ° C. | Fa |
|---|---|---|---|---|---|
| 0.002 | None | 8.9 | 16.8 | 255 | 0.87 |
| | 6 sec @ 245° C. | 8.9 | 11.0 | — | 0.83 |
| | 8 hr @ 210° C. | 7.5 | 7.2 | — | 0.90 |
| 0.026 | None | 8.0 | 13.8 | 256 | 0.70 |
| | 6 sec @ 245° C. | 7.9 | 8.0 | 256 | 0.63 |
| | 2 hr @ 210° C. | 8.0 | 7.0 | 254 | 0.67 |
| 0.056 | None | 8.1 | 12.5 | 258 | 0.66 |

| Undrawn Birefringence | Treated Cord Tenacity, g/d @ 4% FS | LASE-5, g/d @ 4% FS |
|---|---|---|
| 0.002 | 6.9 | 1.2 |
| | — | — |
| | 6.0 | 2.5 |
| 0.026 | 6.6 | 2.5 |
| | 6.6 | 2.5 |
| | 6.3 | 2.8 |
| 0.056 | 6.9 | 2.8 |

What is claimed is:

1. A process for the production of a drawn polyethylene terephthalate yarn which translates to a high tenacity dimensionally stable tire cord comprising:

(a) extruding a molten melt-spinnable polyethylene terephthalate having an intrinsic viscosity of at least about 0.8 through a shaped extrusion orifice having a plurality of openings to form a molten spun yarn;

(b) solidifying gradually said molten spun yarn by passing said molten spun yarn through a solidification zone which comprises (i) a retarded cooling zone and (ii) a cooling zone adjacent said retarded cooling zone where in said cooling zone, said yarn is rapidly cooled and solidified in a gaseous atmosphere;

(c) withdrawing at sufficient speed said solidified yarn from said solidification zone to form a crystalline partially oriented yarn; and (d) hot drawing said crystalline partially oriented yarn at a total draw ratio between about 1.5/1 and about 2.5/1 to produce a drawn yarn having an effective crosslink density (N) between about $10 \times 10^{21}$ and about $20 \times 10^{21}$ crosslinks per cubic centimeter.

2. The process of claim 1 wherein in said step (d), a draw point localizing jet is used.

3. The process of claim 1 wherein in said step (b), said retarded cooling zone comprises a gaseous atmosphere heated at a temperature of 150° C. to 450° C.

4. The process of claim 1 wherein in said step (b), said retarded cooling zone comprises a heated sleeve.

5. The process of claim 4 wherein said heated sleeve is at a temperature of 220° C. to 300° C.

* * * * *